(12) United States Patent
Lunnen et al.

(10) Patent No.: US 6,210,945 B1
(45) Date of Patent: Apr. 3, 2001

(54) **METHOD FOR CLONING AND PRODUCING THE RSAI RESTRICTION ENDONUCLEASE IN *E. COLI* AND PURIFICATION OF THE RECOMBINANT RSAI RESTRICTION ENDONUCLEASE**

(75) Inventors: Keith D. Lunnen, Essex; Richard D. Morgan, Middleton; Timothy Meixsell, Topsfield; Geoffrey G. Wilson, Beverly, all of MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/587,066

(22) Filed: Jun. 2, 2000

(51) Int. Cl.[7] .............................. C12N 9/22; C12N 15/55
(52) U.S. Cl. ................. 435/199; 435/252.33; 435/320.1; 536/23.2
(58) Field of Search .................... 435/199, 320.1, 435/252.33; 536/23.2

(56) References Cited

U.S. PATENT DOCUMENTS

| | | | |
|---|---|---|---|
| 5,200,333 | 4/1993 | Wilson | 435/172.3 |
| 5,246,845 | 9/1993 | Wilson et al. | 435/172.3 |
| 5,498,535 | 3/1996 | Fomenkov et al. | 435/172.3 |

OTHER PUBLICATIONS

Roberts and Macelis, Nucleic Acids Res. 24:223–235 (1996).
Kosykh, et al., Mol. Gen. Genet. 178:717–719 (1980).
Mann, et al., Gene 3:97–112 (1978).
Walder, et al., Proc. Natl. Acad. Sci. USA 78:1503–1507 (1981).
Bougueleret, et al., Nucl. Acids, Res. 12:3659–3676 (1984).
Gingeras and Brooks, Proc. Natl. Acad. Sci. USA 80:402–406 (1983).
Theriault and Roy, Gene 19:355–359 (1982).
Blumenthal, et al., J. Bacteriol. 164:501–509 (1985).
Kiss, et al., Nucl. Acids Res. 13:6403–6421 (1985).
Szomolanyi, et al., Gene 10:219–225 (1980).
Janulaitis, et al., Gene 20:197–204 (1982).
Kiss and Baldauf, Gene 21:111–119 (1983).
Walder, et al., J. Biol Chem. 258:1235–1241 (1983).
Fomenkov, et al., Nucleic Acids Res. 22:2399–2403 (1994).
Lynn, et al., J. Bacteriol. 142:380–383 (1980).
Ives, et al., J. Bacteriol. 174:7194–7201 (1992).
Sohail, et al., Gene 157:227–228 (1995)
Bult, et al., Science 273:1058–1073 (1996).

*Primary Examiner*—Charles L. Patterson, Jr.
(74) *Attorney, Agent, or Firm*—Gregory D. Williams

(57) ABSTRACT

RsaI, a restriction enzyme from the bacterium *Rhodopseudomonas sphaeroides*, recognizes the DNA sequence 5'-GTAC-3'. Because RsaI is commercially valuable, we sought to overproduce it by cloning the genes for RsaI and its accompanying, modification, enzyme. The 'methylase-selection' method, the customary procedure for cloning restriction and modification genes, was applied to RsaI. The method yielded clones containing the methylase gene (rsaIM), but none containing both the methylase gene and the restriction gene (rsaIR). Inverse-PCR was then used to recover sections of the DNA downstream of rsaIM. These sections were sequenced, and the sequences were joined in silico to reveal the gene organization of the RsaI R-M system. By comparing the coding potential of the DNA with the N-terminal amino acid sequence of the purified RsaI restriction enzyme, we discovered that the RsaI R and M genes, rather than being adjacent-the situation that pertains in most R-M systems-are separated by an intervening gene of unknown function. Based on this information, the rsaIR gene was cloned by PCR instead of methylase-selection. These new clones proved to be highly unstable, however, even in the presence of the rsaIM gene. Various attempts were made to stabilize the gene, but most met with failure. Stability was finally achieved by introducing a second methylase gene, mjaVM, to augment the protection provided by rsaIM, and by tightly controlling the expression of rsaIR using a special two-promoter, anti-sense transcription, expression vector.

6 Claims, 7 Drawing Sheets

FIG. 2A

```
    ATGAACCAGCTCTCCATGTTTGACCGAGTCCAATTCGCAGACTCCTCCGCGACGTTCATT
1   ------------+---------+---------+---------+---------+---------+  60
    M  N  Q  L  S  M  F  D  R  V  Q  F  A  D  S  S  A  T  F  I
    GCTGAGGTAGAAGCCTTCTGCGAGTTCGGTCAACGGACCATCGTGGACAGCCGGGATGGC
61  ------------+---------+---------+---------+---------+---------+ 120
    A  E  V  E  A  F  C  E  F  G  Q  R  T  I  V  D  S  R  D  G
    ATCCCCTACTTCATCAACGAGTTCTGGACTGCTGGGCAGCGTCAGGCCCATTCCATCCAC
121 ------------+---------+---------+---------+---------+---------+ 180
    I  P  Y  F  I  N  E  F  W  T  A  G  Q  R  Q  A  H  S  I  H
    GAGGTATCCTACCGCGCCTGCTTCAAGGCTCAGTTGCCGGAGTTCTTCATCGGGAGACTG
181 ------------+---------+---------+---------+---------+---------+ 240
    E  V  S  Y  R  A  C  F  K  A  Q  L  P  E  F  F  I  G  R  L
    ACAAAGCCCGGAGACGTGGTGTTTGATCCATTCATGGGGCGCGGCACGACCCCGGTTCAG
241 ------------+---------+---------+---------+---------+---------+ 300
    T  K  P  G  D  V  V  F  D  P  F  M  G  R  G  T  T  P  V  Q
    GCTGCGCTGATGGAGCGGCAGGCCTTCGGAAATGACGTGAACCCACTGTCAGTCCTTCTG
301 ------------+---------+---------+---------+---------+---------+ 360
    A  A  L  M  E  R  Q  A  F  G  N  D  V  N  P  L  S  V  L  L
    TCGCGCCCACGGCTGCGGCCAATCACCATTGATGCCGTTGCTGCGGCGCTTCGGTCGGTG
361 ------------+---------+---------+---------+---------+---------+ 420
    S  R  P  R  L  R  P  I  T  I  D  A  V  A  A  A  L  R  S  V
    GACTGGTCGGCTGGTGAGGTCAGGCGTGAGGACCTCTTGGCGTTCTACCATCCGGCCACT
421 ------------+---------+---------+---------+---------+---------+ 480
    D  W  S  A  G  E  V  R  R  E  D  L  L  A  F  Y  H  P  A  T
    TTAAAGAAACTGGAAGCCCTGCGCCTTTGGATTGAGGAGCGCGCGCCACTTGGTTCAACT
481 ------------+---------+---------+---------+---------+---------+ 540
    L  K  K  L  E  A  L  R  L  W  I  E  E  R  A  P  L  G  S  T
    GATGTTGATCCGGTTGCAGACTGGATTCGCATGGTCGCAATCAATCGTTTATCGGGCCAT
541 ------------+---------+---------+---------+---------+---------+ 600
    D  V  D  P  V  A  D  W  I  R  M  V  A  I  N  R  L  S  G  H
    TCACCCGGTTTCTTCTCTGGTCGGTCCATGCCGCCAAACCAAGCCGTGTCCGTAAAGGCG
601 ------------+---------+---------+---------+---------+---------+ 660
    S  P  G  F  F  S  G  R  S  M  P  P  N  Q  A  V  S  V  K  A
    CAACTCAAGATCAATGAAAAGCTCGGTGTATCGCCGCCGGAGCGTGACGTTGCGGGCGTC
661 ------------+---------+---------+---------+---------+---------+ 720
    Q  L  K  I  N  E  K  L  G  V  S  P  P  E  R  D  V  A  G  V
    ATCATCAAAAAGTCAAAGACTCTGTTGAAGGACGGCTGTGCCCCAAGTCAGGTTCAGTCC
721 ------------+---------+---------+---------+---------+---------+ 780
    I  I  K  K  S  K  T  L  L  K  D  G  C  A  P  S  Q  V  Q  S
    AGCCTGCATACGGGTGCTGCTTGGGCCGTTCCCGGCATCCCAGACGCCTCTGTTGACCTG
781 ------------+---------+---------+---------+---------+---------+ 840
    S  L  H  T  G  A  A  W  A  V  P  G  I  P  D  A  S  V  D  L
    ACAGTCACATCCCCGCCGTTTTTGGACATTGTCCAGTATGCCGCTGACAACTGGCTGCGT
841 ------------+---------+---------+---------+---------+---------+ 900
    T  V  T  S  P  P  F  L  D  I  V  Q  Y  A  A  D  N  W  L  R
    TGCTGGTTCGCTGGAATTGAGCCGGAGGCCGTCGCAATCGACATGCACAAGACCGAAGAA
901 ------------+---------+---------+---------+---------+---------+ 960
    C  W  F  A  G  I  E  P  E  A  V  A  I  D  M  H  K  T  E  E
    GCGTGGACTTTGATGGTCAACCGGGTCCTGCGGGAACAGGCCAGAATACTGCGCCCGGGC
961 ------------+---------+---------+---------+---------+---------+ 1020
    A  W  T  L  M  V  N  R  V  L  R  E  Q  A  R  I  L  R  P  G
    GGCTATGTCGCCTTTGAGGTGGGCGAAGTCCGAAATGGCAAGGTGTTGCTTGAGAAGCTA
```

FIG. 2B

```
1021 ----------+---------+---------+---------+---------+---------+ 1080
     G  Y  V  A  F  E  V  G  E  V  R  N  G  K  V  L  L  E  K  L
     GTCTGGCGGGCAGCGGAGGGTCTACCTTTTGAGCGGCTGGGTGTGATGGTGAACGACCAA
1081 ----------+---------+---------+---------+---------+---------+ 1140
     V  W  R  A  A  E  G  L  P  F  E  R  L  G  V  M  V  N  D  Q
     GAGTTCACCAAAACAGCCAATTGCTGGGGCGTGGATAACGGCTCCAAAGGCACCAACACA
1141 ----------+---------+---------+---------+---------+---------+ 1200
     E  F  T  K  T  A  N  C  W  G  V  D  N  G  S  K  G  T  N  T
     AATCGGATTGTTTTGTTGCAGCGGCACTAG
1201 ----------+---------+---------+ 1230
     N  R  I  V  L  L  Q  R  H  *
```

FIG. 3

```
       ATGGAAAGACGTTTTCAACTTCGGTGGGATGAGGAGGAGCTTGCGCGCGCCTTCAAGGTC
  1    ------------+----------+----------+----------+----------+----------+   60
       M  E  R  R  F  Q  L  R  W  D  E  E  E  L  A  R  A  F  K  V
       ACGACAAAGGATGTGCGGGAGTATTTGACTGACGGTCGCCGGGTCTCATTCATCATTGAG
 61    ------------+----------+----------+----------+----------+----------+  120
       T  T  K  D  V  R  E  Y  L  T  D  G  R  R  V  S  F  I  I  E
       CGCCGTCTCATGTGGGAAAACCCCGGCTGGAAGCTCGCTCCATCCGAAGGGGCAGGCTAT
121    ------------+----------+----------+----------+----------+----------+  180
       R  R  L  M  W  E  N  P  G  W  K  L  A  P  S  E  G  A  G  Y
       GACCTTCTGGACCCCGAAGGCGGCATGTGGGAAGTCCGGTCCATCACCCGGCAGGGCGTC
181    ------------+----------+----------+----------+----------+----------+  240
       D  L  L  D  P  E  G  G  M  W  E  V  R  S  I  T  R  Q  G  V
       TATTTCAACCCAAGCAATCAGGTTGGGTCTGGCCGCAAGTTCAACGAGGATGGCTTCCAG
241    ------------+----------+----------+----------+----------+----------+  300
       Y  F  N  P  S  N  Q  V  G  S  G  R  K  F  N  E  D  G  F  Q
       TTGAAAATGAGTGGCATCAAGGGGTTCATCTTGTCCGACATTGTGGGCTTCCCGCTCGTG
301    ------------+----------+----------+----------+----------+----------+  360
       L  K  M  S  G  I  K  G  F  I  L  S  D  I  V  G  F  P  L  V
       GACGTTTACGTTGTCCCCGTTGAGAACGTGCTGCGCTGGCACCAAGCCCGGGCGCTGGGT
361    ------------+----------+----------+----------+----------+----------+  420
       D  V  Y  V  V  P  V  E  N  V  L  R  W  H  Q  A  R  A  L  G
       GCGAATGCGAAGGTGTCCCGCGAGAAGTTCCTGCGTGACATGGTCCGGGACATTCGGCAC
421    ------------+----------+----------+----------+----------+----------+  480
       A  N  A  K  V  S  R  E  K  F  L  R  D  M  V  R  D  I  R  H
       TGA
481    ---  483
       *
```

FIG. 4

```
    GTGCCACGGCAACAGGATCGGATCAAGGAGGCTGTTTTGTCGCGTTTTGACGACTATCTG
1   ------------+---------+---------+---------+---------+---------+  60
    V  P  R  Q  Q  D  R  I  K  E  A  V  L  S  R  F  D  D  Y  L
    ACAGAAGTGCAGCAGCGAATGGGCCTTGTGCCCATCAACTTAATCAGGACGTGGACTGCT
61  ------------+---------+---------+---------+---------+---------+  120
    T  E  V  Q  Q  R  M  G  L  V  P  I  N  L  I  R  T  W  T  A
    GCTGAAATCACTTCGGTTGAATTGGCAATCCGAACTGCCGTGGCAGCAAGTCAAATTGTG
121 ------------+---------+---------+---------+---------+---------+  180
    A  E  I  T  S  V  E  L  A  I  R  T  A  V  A  A  S  Q  I  V
    GGAATGGTGATCCCTAATTTTGTTGGCACCAATCAGGCAAAAGGGAACAAAGCCGCAGAC
181 ------------+---------+---------+---------+---------+---------+  240
    G  M  V  I  P  N  F  V  G  T  N  Q  A  K  G  N  K  A  A  D
    TTCTTTATTGCGACAATCCCGCCTCATCTTCCTGCAAACAACAGCATAGTTGCCGCCCGA
241 ------------+---------+---------+---------+---------+---------+  300
    F  F  I  A  T  I  P  P  H  L  P  A  N  N  S  I  V  A  A  R
    GGTGCAGGCTATCCAGACCGCCTTTTCGTGTCTGGGGCCACAAGGCATTGCATGGAATTC
301 ------------+---------+---------+---------+---------+---------+  360
    G  A  G  Y  P  D  R  L  F  V  S  G  A  T  R  H  C  M  E  F
    AAGGCGACCTCAAATTGGCAAGATGGTGATCCAAACAGAAGGGTCCTGACCAGCGCCCCG
361 ------------+---------+---------+---------+---------+---------+  420
    K  A  T  S  N  W  Q  D  G  D  P  N  R  R  V  L  T  S  A  P
    ACCAAAATGATCCGTCTGGTAAACTCACGTCAAGTTGGGGTTGCGCCGAACCATGTCCCA
421 ------------+---------+---------+---------+---------+---------+  480
    T  K  M  I  R  L  V  N  S  R  Q  V  G  V  A  P  N  H  V  P
    GCACACCTGATCTGCACTGTCCTTTACAGTGAACAGCAATCATCTGTGCAAGGCGTCCGT
481 ------------+---------+---------+---------+---------+---------+  540
    A  H  L  I  C  T  V  L  Y  S  E  Q  Q  S  S  V  Q  G  V  R
    CTAGATTTTCTTGAGCCAGACTCTGAGGTAAACATTCGATTGGAGGCCTCAACCTCTCAA
541 ------------+---------+---------+---------+---------+---------+  600
    L  D  F  L  E  P  D  S  E  V  N  I  R  L  E  A  S  T  S  Q
    CGGCTACTTGCGATGGGCACTCAGCAGAGGTTCATCTACCCCTAG
601 ------------+---------+---------+---------+-----  645
    R  L  L  A  M  G  T  Q  Q  R  F  I  Y  P  *
```

Note: rsaIR cloned at BsaAI site

SEQUENCE LISTING

<160> NUMBER OF SEQ ID NOS: 20

<210> SEQ ID NO 1
<211> LENGTH: 1230
<212> TYPE: DNA
<213> ORGANISM: rhodopseudomonas sphaeroides
<220> FEATURE:
<221> NAME/KEY: CDS
<222> LOCATION: (1)..(1230)

<400> SEQUENCE: 1

```
atg aac cag ctc tcc atg ttt gac cga gtc caa ttc gca gac tcc tcc      48
Met Asn Gln Leu Ser Met Phe Asp Arg Val Gln Phe Ala Asp Ser Ser
 1               5                  10                  15 gcg acg ttc att gct gag gta gaa gcc ttc tgc gag ttc ggt caa cgg      96
Ala Thr Phe Ile Ala Glu Val Glu Ala Phe Cys Glu Phe Gly Gln Arg
             20                  25                  30
```

```
acc atc gtg gac agc cgg gat ggc atc ccc tac ttc atc aac gag ttc      144
Thr Ile Val Asp Ser Arg Asp Gly Ile Pro Tyr Phe Ile Asn Glu Phe
         35                  40                  45 tgg act gct ggg cag cgt cag gcc cat tcc atc cac gag gta tcc tac      192
Trp Thr Ala Gly Gln Arg Gln Ala His Ser Ile His Glu Val Ser Tyr
     50                  55                  60 cgc gcc tgc ttc aag gct cag ttg ccg gag ttc ttc atc ggg aga ctg      240
Arg Ala Cys Phe Lys Ala Gln Leu Pro Glu Phe Phe Ile Gly Arg Leu
 65                  70                  75                  80 aca aag ccc gga gac gtg gtg ttt gat cca ttc atg ggg cgc ggc acg      288
Thr Lys Pro Gly Asp Val Val Phe Asp Pro Phe Met Gly Arg Gly Thr
                 85                  90                  95 acc ccg gtt cag gct gcg ctg atg gag cgg cag gcc ttc gga aat gac      336
Thr Pro Val Gln Ala Ala Leu Met Glu Arg Gln Ala Phe Gly Asn Asp
            100                 105                 110 gtg aac cca ctg tca gtc ctt ctg tcg cgc cca cgg ctg cgg cca atc      384
Val Asn Pro Leu Ser Val Leu Leu Ser Arg Pro Arg Leu Arg Pro Ile
        115                 120                 125 acc att gat gcc gtt gct gcg gcg ctt cgg tcg gtg gac tgg tcg gct      432
Thr Ile Asp Ala Val Ala Ala Ala Leu Arg Ser Val Asp Trp Ser Ala
    130                 135                 140 ggt gag gtc agg cgt gag gac ctc ttg gcg ttc tac cat ccg gcc act      480
Gly Glu Val Arg Arg Glu Asp Leu Leu Ala Phe Tyr His Pro Ala Thr
145                 150                 155                 160 tta aag aaa ctg gaa gcc ctg cgc ctt tgg att gag gag cgc gcg cca      528
Leu Lys Lys Leu Glu Ala Leu Arg Leu Trp Ile Glu Glu Arg Ala Pro
                165                 170                 175 ctt ggt tca act gat gtt gat ccg gtt gca gac tgg att cgc atg gtc      576
Leu Gly Ser Thr Asp Val Asp Pro Val Ala Asp Trp Ile Arg Met Val
            180                 185                 190 gca atc aat cgt tta tcg ggc cat tca ccc ggt ttc ttc tct ggt cgg      624
Ala Ile Asn Arg Leu Ser Gly His Ser Pro Gly Phe Phe Ser Gly Arg
        195                 200                 205 tcc atg ccg cca aac caa gcc gtg tcc gta aag gcg caa ctc aag atc      672
Ser Met Pro Pro Asn Gln Ala Val Ser Val Lys Ala Gln Leu Lys Ile
    210                 215                 220 aat gaa aag ctc ggt gta tcg ccg ccg gag cgt gac gtt gcg ggc gtc      720
Asn Glu Lys Leu Gly Val Ser Pro Pro Glu Arg Asp Val Ala Gly Val
225                 230                 235                 240 atc atc aaa aag tca aag act ctg ttg aag gac ggc tgt gcc cca agt      768
Ile Ile Lys Lys Ser Lys Thr Leu Leu Lys Asp Gly Cys Ala Pro Ser
                245                 250                 255 cag gtt cag tcc agc ctg cat acg ggt gct gct tgg gcc gtt ccc ggc      816
Gln Val Gln Ser Ser Leu His Thr Gly Ala Ala Trp Ala Val Pro Gly
            260                 265                 270 atc cca gac gcc tct gtt gac ctg aca gtc aca tcc ccg ccg ttt ttg      864
Ile Pro Asp Ala Ser Val Asp Leu Thr Val Thr Ser Pro Pro Phe Leu
        275                 280                 285 gac att gtc cag tat gcc gct gac aac tgg ctg cgt tgc tgg ttc gct      912
Asp Ile Val Gln Tyr Ala Ala Asp Asn Trp Leu Arg Cys Trp Phe Ala
    290                 295                 300 gga att gag ccg gag gcc gtc gca atc gac atg cac aag acc gaa gaa      960
Gly Ile Glu Pro Glu Ala Val Ala Ile Asp Met His Lys Thr Glu Glu
305                 310                 315                 320 gcg tgg act ttg atg gtc aac cgg gtc ctg cgg gaa cag gcc aga ata     1008
Ala Trp Thr Leu Met Val Asn Arg Val Leu Arg Glu Gln Ala Arg Ile
                325                 330                 335 ctg cgc ccg ggc ggc tat gtc gcc ttt gag gtg ggc gaa gtc cga aat     1056
Leu Arg Pro Gly Gly Tyr Val Ala Phe Glu Val Gly Glu Val Arg Asn
```

-continued

```
            340                 345                 350
ggc aag gtg ttg ctt gag aag cta gtc tgg cgg gca gcg gag ggt cta      1104
Gly Lys Val Leu Leu Glu Lys Leu Val Trp Arg Ala Ala Glu Gly Leu
        355                 360                 365 cct ttt gag cgg ctg ggt gtg atg gtg aac gac caa gag ttc acc aaa      1152
Pro Phe Glu Arg Leu Gly Val Met Val Asn Asp Gln Glu Phe Thr Lys
370                 375                 380 aca gcc aat tgc tgg ggc gtg gat aac ggc tcc aaa ggc acc aac aca      1200
Thr Ala Asn Cys Trp Gly Val Asp Asn Gly Ser Lys Gly Thr Asn Thr
385                 390                 395                 400 aat cgg att gtt ttg ttg cag cgg cac tag                              1230
Asn Arg Ile Val Leu Leu Gln Arg His
                405                 410

<210> SEQ ID NO 2
<211> LENGTH: 409
<212> TYPE: PRT
<213> ORGANISM: rhodopseudomonas sphaeroides

<400> SEQUENCE: 2

Met Asn Gln Leu Ser Met Phe Asp Arg Val Gln Phe Ala Asp Ser Ser
  1               5                  10                  15

Ala Thr Phe Ile Ala Glu Val Glu Ala Phe Cys Glu Phe Gly Gln Arg
                 20                  25                  30

Thr Ile Val Asp Ser Arg Asp Gly Ile Pro Tyr Phe Ile Asn Glu Phe
             35                  40                  45

Trp Thr Ala Gly Gln Arg Gln Ala His Ser Ile His Glu Val Ser Tyr
         50                  55                  60

Arg Ala Cys Phe Lys Ala Gln Leu Pro Glu Phe Phe Ile Gly Arg Leu
 65                  70                  75                  80

Thr Lys Pro Gly Asp Val Val Phe Asp Pro Phe Met Gly Arg Gly Thr
                 85                  90                  95

Thr Pro Val Gln Ala Ala Leu Met Glu Arg Gln Ala Phe Gly Asn Asp
                100                 105                 110

Val Asn Pro Leu Ser Val Leu Leu Ser Arg Pro Arg Leu Arg Pro Ile
            115                 120                 125

Thr Ile Asp Ala Val Ala Ala Leu Arg Ser Val Asp Trp Ser Ala
        130                 135                 140

Gly Glu Val Arg Arg Glu Asp Leu Leu Ala Phe Tyr His Pro Ala Thr
145                 150                 155                 160

Leu Lys Lys Leu Glu Ala Leu Arg Leu Trp Ile Glu Glu Arg Ala Pro
                165                 170                 175

Leu Gly Ser Thr Asp Val Asp Pro Val Ala Asp Trp Ile Arg Met Val
            180                 185                 190

Ala Ile Asn Arg Leu Ser Gly His Ser Pro Gly Phe Phe Ser Gly Arg
        195                 200                 205

Ser Met Pro Pro Asn Gln Ala Val Ser Val Lys Ala Gln Leu Lys Ile
210                 215                 220

Asn Glu Lys Leu Gly Val Ser Pro Pro Glu Arg Asp Val Ala Gly Val
225                 230                 235                 240

Ile Ile Lys Lys Ser Lys Thr Leu Leu Lys Asp Gly Cys Ala Pro Ser
                245                 250                 255

Gln Val Gln Ser Ser Leu His Thr Gly Ala Ala Trp Ala Val Pro Gly
            260                 265                 270

Ile Pro Asp Ala Ser Val Asp Leu Thr Val Thr Ser Pro Pro Phe Leu
        275                 280                 285
```

```
Asp Ile Val Gln Tyr Ala Ala Asp Asn Trp Leu Arg Cys Trp Phe Ala
    290                 295                 300
Gly Ile Glu Pro Glu Ala Val Ala Ile Asp Met His Lys Thr Glu Glu
305                 310                 315                 320
Ala Trp Thr Leu Met Val Asn Arg Val Leu Arg Glu Gln Ala Arg Ile
                325                 330                 335
Leu Arg Pro Gly Gly Tyr Val Ala Phe Glu Val Gly Glu Val Arg Asn
            340                 345                 350
Gly Lys Val Leu Glu Lys Leu Val Trp Arg Ala Ala Glu Gly Leu
        355                 360                 365
Pro Phe Glu Arg Leu Gly Val Met Val Asn Asp Gln Glu Phe Thr Lys
370                 375                 380
Thr Ala Asn Cys Trp Gly Val Asp Asn Gly Ser Lys Gly Thr Asn Thr
385                 390                 395                 400
Asn Arg Ile Val Leu Leu Gln Arg His
                405
```

```
<210> SEQ ID NO 3
<211> LENGTH: 483
<212> TYPE: DNA
<213> ORGANISM: rhodopseudomonas sphaeroides
<220> FEATURE:
<221> NAME/KEY: CDS
<222> LOCATION: (1)..(483)

<400> SEQUENCE: 3
```

```
atg gaa aga cgt ttt caa ctt cgg tgg gat gag gag gag ctt gcg cgc      48
Met Glu Arg Arg Phe Gln Leu Arg Trp Asp Glu Glu Glu Leu Ala Arg
  1               5                  10                  15 gcc ttc aag gtc acg aca aag gat gtg cgg gag tat ttg act gac ggt      96
Ala Phe Lys Val Thr Thr Lys Asp Val Arg Glu Tyr Leu Thr Asp Gly
             20                  25                  30 cgc cgg gtc tca ttc atc att gag cgc cgt ctc atg tgg gaa aac ccc    144
Arg Arg Val Ser Phe Ile Ile Glu Arg Arg Leu Met Trp Glu Asn Pro
         35                  40                  45 ggc tgg aag ctc gct cca tcc gaa ggg gca ggc tat gac ctt ctg gac    192
Gly Trp Lys Leu Ala Pro Ser Glu Gly Ala Gly Tyr Asp Leu Leu Asp
     50                  55                  60 ccc gaa ggc ggc atg tgg gaa gtc cgg tcc atc acc cgg cag ggc gtc    240
Pro Glu Gly Gly Met Trp Glu Val Arg Ser Ile Thr Arg Gln Gly Val
 65                  70                  75                  80 tat ttc aac cca agc aat cag gtt ggg tct ggc cgc aag ttc aac gag    288
Tyr Phe Asn Pro Ser Asn Gln Val Gly Ser Gly Arg Lys Phe Asn Glu
                 85                  90                  95 gat ggc ttc cag ttg aaa atg agt ggc atc aag ggg ttc atc ttg tcc    336
Asp Gly Phe Gln Leu Lys Met Ser Gly Ile Lys Gly Phe Ile Leu Ser
            100                 105                 110 gac att gtg ggc ttc ccg ctc gtg gac gtt tac gtt gtc ccc gtt gag    384
Asp Ile Val Gly Phe Pro Leu Val Asp Val Tyr Val Val Pro Val Glu
        115                 120                 125 aac gtg ctg cgc tgg cac caa gcc cgg gcg ctg ggt gcg aat gcg aag    432
Asn Val Leu Arg Trp His Gln Ala Arg Ala Leu Gly Ala Asn Ala Lys
    130                 135                 140 gtg tcc cgc gag aag ttc ctg cgt gac atg gtc cgg gac att cgg cac    480
Val Ser Arg Glu Lys Phe Leu Arg Asp Met Val Arg Asp Ile Arg His
145                 150                 155                 160 tga                                                                 483
```

```
<210> SEQ ID NO 4
<211> LENGTH: 160
<212> TYPE: PRT
<213> ORGANISM: rhodopseudomonas sphaeroides

<400> SEQUENCE: 4

Met Glu Arg Arg Phe Gln Leu Arg Trp Asp Glu Glu Leu Ala Arg
 1               5                  10                  15

Ala Phe Lys Val Thr Thr Lys Asp Val Arg Glu Tyr Leu Thr Asp Gly
                20                  25                  30

Arg Arg Val Ser Phe Ile Ile Glu Arg Leu Met Trp Glu Asn Pro
            35                  40                  45

Gly Trp Lys Leu Ala Pro Ser Glu Gly Ala Gly Tyr Asp Leu Leu Asp
     50                  55                  60

Pro Glu Gly Gly Met Trp Glu Val Arg Ser Ile Thr Arg Gln Gly Val
 65                  70                  75                  80

Tyr Phe Asn Pro Ser Asn Gln Val Gly Ser Gly Arg Lys Phe Asn Glu
                85                  90                  95

Asp Gly Phe Gln Leu Lys Met Ser Gly Ile Lys Gly Phe Ile Leu Ser
                100                 105                 110

Asp Ile Val Gly Phe Pro Leu Val Asp Val Tyr Val Val Pro Val Glu
            115                 120                 125

Asn Val Leu Arg Trp His Gln Ala Arg Ala Leu Gly Ala Asn Ala Lys
        130                 135                 140

Val Ser Arg Glu Lys Phe Leu Arg Asp Met Val Arg Asp Ile Arg His
145                 150                 155                 160

<210> SEQ ID NO 5
<211> LENGTH: 645
<212> TYPE: DNA
<213> ORGANISM: rhodopseudomonas sphaeroides
<220> FEATURE:
<221> NAME/KEY: CDS
<222> LOCATION: (1)..(645)

<400> SEQUENCE: 5 gtg cca cgg caa cag gat cgg atc aag gag gct gtt ttg tcg cgt ttt      48
Val Pro Arg Gln Gln Asp Arg Ile Lys Glu Ala Val Leu Ser Arg Phe
 1               5                  10                  15 gac gac tat ctg aca gaa gtg cag cag cga atg ggc ctt gtg ccc atc      96
Asp Asp Tyr Leu Thr Glu Val Gln Gln Arg Met Gly Leu Val Pro Ile
                20                  25                  30 aac tta atc agg acg tgg act gct gct gaa atc act tcg gtt gaa ttg     144
Asn Leu Ile Arg Thr Trp Thr Ala Ala Glu Ile Thr Ser Val Glu Leu
            35                  40                  45 gca atc cga act gcc gtg gca gca agt caa att gtg gga atg gtg atc     192
Ala Ile Arg Thr Ala Val Ala Ala Ser Gln Ile Val Gly Met Val Ile
     50                  55                  60 cct aat ttt gtt ggc acc aat cag gca aaa ggg aac aaa gcc gca gac     240
Pro Asn Phe Val Gly Thr Asn Gln Ala Lys Gly Asn Lys Ala Ala Asp
 65                  70                  75                  80 ttc ttt att gcg aca atc ccg cct cat ctt cct gca aac aac agc ata     288
Phe Phe Ile Ala Thr Ile Pro Pro His Leu Pro Ala Asn Asn Ser Ile
                85                  90                  95 gtt gcc gcc cga ggt gca ggc tat cca gac cgc ctt ttc gtg tct ggg     336
Val Ala Ala Arg Gly Ala Gly Tyr Pro Asp Arg Leu Phe Val Ser Gly
                100                 105                 110 gcc aca agg cat tgc atg gaa ttc aag gcg acc tca aat tgg caa gat     384
Ala Thr Arg His Cys Met Glu Phe Lys Ala Thr Ser Asn Trp Gln Asp
            115                 120                 125
```

-continued

```
ggt gat cca aac aga agg gtc ctg acc agc gcc ccg acc aaa atg atc      432
Gly Asp Pro Asn Arg Arg Val Leu Thr Ser Ala Pro Thr Lys Met Ile
    130                 135                 140 cgt ctg gta aac tca cgt caa gtt ggg gtt gcg ccg aac cat gtc cca      480
Arg Leu Val Asn Ser Arg Gln Val Gly Val Ala Pro Asn His Val Pro
145                 150                 155                 160 gca cac ctg atc tgc act gtc ctt tac agt gaa cag caa tca tct gtg      528
Ala His Leu Ile Cys Thr Val Leu Tyr Ser Glu Gln Gln Ser Ser Val
                165                 170                 175 caa ggc gtc cgt cta gat ttt ctt gag cca gac tct gag gta aac att      576
Gln Gly Val Arg Leu Asp Phe Leu Glu Pro Asp Ser Glu Val Asn Ile
            180                 185                 190 cga ttg gag gcc tca acc tct caa cgg cta ctt gcg atg ggc act cag      624
Arg Leu Glu Ala Ser Thr Ser Gln Arg Leu Leu Ala Met Gly Thr Gln
        195                 200                 205 cag agg ttc atc tac ccc tag                                          645
Gln Arg Phe Ile Tyr Pro
    210                 215
```

<210> SEQ ID NO 6
<211> LENGTH: 214
<212> TYPE: PRT
<213> ORGANISM: rhodopseudomonas sphaeroides

<400> SEQUENCE: 6

```
Val Pro Arg Gln Gln Asp Arg Ile Lys Glu Ala Val Leu Ser Arg Phe
 1               5                  10                  15

Asp Asp Tyr Leu Thr Glu Val Gln Gln Arg Met Gly Leu Val Pro Ile
                20                  25                  30

Asn Leu Ile Arg Thr Trp Thr Ala Glu Ile Thr Ser Val Glu Leu
            35                  40                  45

Ala Ile Arg Thr Ala Val Ala Ala Ser Gln Ile Val Gly Met Val Ile
        50                  55                  60

Pro Asn Phe Val Gly Thr Asn Gln Ala Lys Gly Asn Lys Ala Ala Asp
65                  70                  75                  80

Phe Phe Ile Ala Thr Ile Pro Pro His Leu Pro Ala Asn Asn Ser Ile
                85                  90                  95

Val Ala Ala Arg Gly Ala Gly Tyr Pro Asp Arg Leu Phe Val Ser Gly
            100                 105                 110

Ala Thr Arg His Cys Met Glu Phe Lys Ala Thr Ser Asn Trp Gln Asp
        115                 120                 125

Gly Asp Pro Asn Arg Arg Val Leu Thr Ser Ala Pro Thr Lys Met Ile
    130                 135                 140

Arg Leu Val Asn Ser Arg Gln Val Gly Val Ala Pro Asn His Val Pro
145                 150                 155                 160

Ala His Leu Ile Cys Thr Val Leu Tyr Ser Glu Gln Gln Ser Ser Val
                165                 170                 175

Gln Gly Val Arg Leu Asp Phe Leu Glu Pro Asp Ser Glu Val Asn Ile
            180                 185                 190

Arg Leu Glu Ala Ser Thr Ser Gln Arg Leu Leu Ala Met Gly Thr Gln
        195                 200                 205

Gln Arg Phe Ile Tyr Pro
    210
```

<210> SEQ ID NO 7
<211> LENGTH: 23
<212> TYPE: PRT

<213> ORGANISM: rhodopseudomonas sphaeroides

<400> SEQUENCE: 7

Met Glu Arg Arg Phe Pro Leu Arg Trp Asp Glu Glu Leu Ala Arg
1               5                   10                  15

Ala Phe Lys Val Thr Thr Lys
            20

<210> SEQ ID NO 8
<211> LENGTH: 26
<212> TYPE: PRT
<213> ORGANISM: rhodopseudomonas sphaeroides

<400> SEQUENCE: 8

Met Ala Arg Glu Ile Pro Asp Leu Gln Ala Val Val Arg Thr Gly Thr
1               5                   10                  15

Gly Lys Gly Ala Ala Arg Gln Ala Arg Xaa
            20                  25

<210> SEQ ID NO 9
<211> LENGTH: 36
<212> TYPE: DNA
<213> ORGANISM: rhodopseudomonas sphaeroides

<400> SEQUENCE: 9
aggtccggat ccatcggatt gttttgttgc agcggc                         36

<210> SEQ ID NO 10
<211> LENGTH: 36
<212> TYPE: DNA
<213> ORGANISM: rhodopseudomonas sphaeroides

<400> SEQUENCE: 10
aggtccctgc agttggtgcc tttggagccg ttatcc                         36

<210> SEQ ID NO 11
<211> LENGTH: 36
<212> TYPE: DNA
<213> ORGANISM: rhodopseudomonas sphaeroides

<400> SEQUENCE: 11
aggtccctgc agttggtgcc tttggagccg ttatcc                         36

<210> SEQ ID NO 12
<211> LENGTH: 24
<212> TYPE: DNA
<213> ORGANISM: rhodopseudomonas sphaeroides

<400> SEQUENCE: 12
tgcgcgcgcc ttcaaggtca cgac                                      24

<210> SEQ ID NO 13
<211> LENGTH: 60
<212> TYPE: DNA
<213> ORGANISM: rhodopseudomonas sphaeroides

<400> SEQUENCE: 13
cggggtaccg catgcaagga ggtttaaaat atgaaccagc tctccatgtt tgaccgagtc   60

<210> SEQ ID NO 14
<211> LENGTH: 45
<212> TYPE: DNA
<213> ORGANISM: rhodopseudomonas sphaeroides -continued

```
<400> SEQUENCE: 14
tggcggccgg gatcctcact agtgccgctg caacaaaaca atccg                45

<210> SEQ ID NO 15
<211> LENGTH: 51
<212> TYPE: DNA
<213> ORGANISM: rhodopseudomonas sphaeroides

<400> SEQUENCE: 15
gttggatccg taattaagga ggtaattcat atggagataa ataaaatcta c         51

<210> SEQ ID NO 16
<211> LENGTH: 33
<212> TYPE: DNA
<213> ORGANISM: rhodopseudomonas sphaeroides

<400> SEQUENCE: 16
gttgaatccg tcgactattt aaataaatgc atc                             33

<210> SEQ ID NO 17
<211> LENGTH: 54
<212> TYPE: DNA
<213> ORGANISM: rhodopseudomonas sphaeroides

<400> SEQUENCE: 17
ttgttctgca gtaaggaggt ttaaaatatg gaaagacgtt ttcaacttcg gtgg       54

<210> SEQ ID NO 18
<211> LENGTH: 36
<212> TYPE: DNA
<213> ORGANISM: rhodopseudomonas sphaeroides

<400> SEQUENCE: 18
ttgggatcct cagtgccgaa tgtcccggac catgtc                          36

<210> SEQ ID NO 19
<211> LENGTH: 62
<212> TYPE: DNA
<213> ORGANISM: rhodopseudomonas sphaeroides

<400> SEQUENCE: 19
tggggtctag aggaggtaac atatggaaag acgttttcaa cttcggtggg atgaggagga 60
gc                                                               62

<210> SEQ ID NO 20
<211> LENGTH: 42
<212> TYPE: DNA
<213> ORGANISM: rhodopseudomonas sphaeroides

<400> SEQUENCE: 20
ttgggtctcg agtcagtgcc gaatgtcccg gaccatgtca cg                   42
```

METHOD FOR CLONING AND PRODUCING THE RSAI RESTRICTION ENDONUCLEASE IN *E. COLI* AND PURIFICATION OF THE RECOMBINANT RSAI RESTRICTION ENDONUCLEASE

BACKGROUND OF THE INVENTION

The present invention relates to recombinant DNA that encodes the RsaI restriction endonuclease, as well as the RsaI methylase, and to the production of the RsaI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into fragments for molecular cloning and gene characterization.

Restriction endonucleases act by binding to particular sequences of nucleotides (the 'recognition sequence') along the DNA molecule. Once bound, they cleave the DNA molecule within, to one side of, or to both sides of the recognition sequence. Different restriction endonucleases recognize and cleave different nucleotide sequences. Over two hundred restriction endonucleases with unique specificities have been identified among thousands of bacterial species that have been examined (Roberts and Macelis, *Nucl. Acids Res.* 24:223–235, (1996)).

Restriction endonucleases are named according to the bacteria from which they derive. Thus, the bacterium *Deinococcus radiophilus* for example, produces three different restriction endonucleases, named DraI, DraII and DraIII. These enzymes recognize and cleave the sequences 5'-TTTAAA-3', 5'-PuGGNCCPy-3' and 5'-CACNNNGTG-3' respectively. *Escherichia coli* RY13, on the other hand, produces only one restriction enzyme, EcoRI, which recognizes the sequence 5' GAATTC 3'.

Restriction endonucleases usually occur together with one or more companion enzymes termed methyltransferase, the whole forming a restriction-modification (R-M) system. Methyltransferases are complementary to the restriction endonuclease they accompany and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one of the nucleotides within the sequence by the addition of a methyl group to form 5-methylcytosine, N4-methylcytosine, or N6-methyladenine. Following methylation, the recognition sequence is no longer cleaved by the cognate restriction endonuclease. The DNA of a bacterial cell is always fully modified by virtue of the activity of its modification methylase(s), and therefore it is completely insensitive to the presence of the restriction endonuclease. It is only unmodified, and therefore identifiably foreign DNA, that is sensitive to restriction endonuclease recognition and cleavage.

With the advent of recombinant DNA technology, it is possible to clone genes and overproduce the enzymes they encode in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used resistance to bacteriophage infection as a means of identifying or selecting restriction endonuclease clones (EcoRII: Kosykh et al., *Mol. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985)).

A third approach to clone R-M systems is by selection for an active methylase gene (U.S. Pat. No. 5,200,333 and BsuRI: Kiss et al., *Nucl. Acids. Res.* 13:6403–6421, (1985)). Since R and M genes are usually closely linked, both genes can often be cloned simultaneously by selecting for only one. Selection for the M gene does not always yield a complete restriction system however, but often instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983); and MspI: Walder et al., *J. Biol. Chem.* 258:1235–1241, (1983)).

Another approach is to clone R-M Systems in *E.coli* by making use of the fact that certain modification genes, when cloned into a new host and adequately expressed, enable the host to tolerate the presence of a different restriction gene (Wilson et al; U.S. Pat. No. 5,246,845).

A more recent method, the "endo-blue method", has been described for direct cloning of restriction endonuclease genes in E. coli based on the indicator strain of *E. coli* containing the dinD::lacZ fusion (Fomenkov et al., U.S. Pat. No. 5,498,535; Fomenkov et al., *Nucl. Acids Res.* 22:2399–2403, (1994)). This method utilizes the *E. coli* SOS response following DNA damages caused by restriction endonucleases or non-specific nucleases. A number of thermostable nuclease genes (Tth111I, BsoBI, Tf nuclease) have been cloned by this method (U.S. Pat. No. 5,498,535).

Because purified restriction endonucleases, and to a lesser extent modification methylases, are useful tools for manipulating DNA molecules in the laboratory, there is a commercial incentive to create bacterial strains through recombinant DNA techniques that produce these enzymes in large quantities. Such overexpression strains also simplify the task of enzyme purification.

SUMMARY OF THE INVENTION

The methylase selection method was used to clone the RsaI methylase gene (rsaIM) from *Rhodopseudomonas sphaeroides* (NEB (New England Biolabs, Beverly, Mass.) Culture Collection #233, (Lynn, et al., *J. Bacteriol.* 142:380–383 (1980)) into the *E.coli* plasmid vector pBR322. Subcloning, deletion mapping, and DNA sequencing verified the location of the inserted RsaI methylase gene (ORF1) and revealed the presence of a second incomplete converging open reading frame (ORF2).

Because methylase endonuclease genes usually occur next to each other in bacterial DNA, ORF2 was assumed to be the rsaIR gene and efforts were made to clone the missing portion of ORF2. Southern blots revealed that Bc/I-, BstYI-, and PstI-fragments could potentially contain rsaIM as well as enough adjacent DNA to include the whole ORF2. Methylase selection on de novo libraries made with Bc/I and BstYI, as well as with size-fractionated, gel-purified, PstI-digested, chromosomal DNA failed to yield any RsaI methylase clones whatsoever, suggesting that these fragments were perhaps toxic in *E.coli*.

Native RsaI restriction endonuclease was purified to near homogeneity from a *Rhodopseudomonas sphaeroides* cell extract. Two proteins of approximately 18 kDa and 22 kDa were found to be present in the prep by SDS-PAGE gel analysis. The N-terminal amino acid sequences of both of these proteins were determined, and they were used to synthesize primers for PCR of a fragment containing rsaIM and the converging ORF2. These PCR attempts also failed to yield the desired clone.

Finally, inverse PCR, was used to isolate the adjacent chromosomal DNA and this fragment was cloned into both pCAB16 and pUC19 and sequenced. Two complete open reading frames (ORFs) were found downstream of the rsaIM gene (ORF1) including the above mentioned second converging ORF (ORF2) and an additional ORF (ORF3). The derived amino acid sequences of the proteins encoded by ORF2 and ORF3 did not match any of the known proteins in the Genbank data base which is indicative of a potential restriction endonuclease. However, amino acid sequence encoded by the beginning of the third ORF (ORF3) matched exactly the N-terminal amino acid sequence of the 18 kDa endonuclease candidate protein. The amino acid sequence encoded by the beginning ORF2 did not match the N-terminal sequence of either the 18 kDa or the 22 kDa protein. This indicated that ORF3 was probably the rsaIR gene, and not ORF2, and that the RsaI endonuclease protein was 18 kDa in size.

In most R-M systems, the restriction and modification genes occur side-by-side with no other genes between them. The RsaI R-M system appears to be unusual in that a gene of unknown function, ORF2, separates the R and M genes. Intervening genes have been found in a few R-M systems, but in all cases the functions of these intervening genes are known. For example, in the BsuRI R-M system, a vsr-type mismatch repair (V) gene separates the bsuRI R and M genes (J. Barsomian and G. Wilson, unpublished). In the AhdI R-M system, a DNA sequence-specificity (S) gene separates the ahdI R and M genes (K. Lunnen, T. Cui and G. Wilson, unpublished). And in the BamHI R-M system, a regulatory, or C, gene separates the bamHI R and M genes (Ives, et al., *J. Bacteriol.*, 174:7194–7201 (1992); Sohail, et al., *Gene* 157:227–228 (1995)). The intervening gene in the RsaI R-M system is different from these other intervening genes, and it is unique. The protein encoded by the gene resembles neither V, C, or S, proteins, nor any other protein in the GenBank database.

*Methanococcus jannascii* encodes an isoschizomer of RsaI designated MjaV. The R and M genes of the MjaV R-M system occur in a different, opposing, orientation to the genes of the RsaI R-M system, but they too are separated by a unique gene. The protein encoded by this gene does not resemble the corresponding intervening protein of the RsaI system, and it is also unique in that it resembles neither V, C, or S, proteins, nor any other protein in the GenBank database. (Bult, et al. *Science* 273:1058–1073, (1996); Morgan, R., Posfai, J., Patti, J., Roberts, R.J, unpublished, New England Biolabs; R. Morgan, K. Lunnen, and G. Wilson, unpublished, New England Biolabs)).

Attempts to clone an active RsaI restriction gene (ORF3) directly into pRRS (Skoglund et al, *Gene*, 88:1–5 (1990)) by transforming into a pre-modified *E.coli* host containing the RsaI methylase gene failed. Only two pRRS-rsaIR clones, #13 and #14 with reduced RsaI endonuclease activity were isolated from a RsaI methylase pre-modified *E.coli* host. The same ligation transformed into a MjaV methylase pre-modified *E. coli* host also failed to yield any clones. DNA sequencing of reduced activity clone #14 revealed a deletion mutation of T at the start codon (ATG) which most likely truncated the RsaI endonuclease at the N-terminal end due to a delayed GTG start codon downstream. The truncated RsaI endonuclease clones revealed low or no activity when grown at 30° C. verses a sustained RsaI partial endonuclease activity for cultures grown at 37° C.

An rsaIR PCR fragment from *Rhodopseudomonas sphaeroides* chromosomal DNA was then cloned and sequenced after ligation into pCAB16 at a BsaAI site. pCAB16 is a pUC18 derivative containing the active mspIR gene cloned into the polylinker of pUC18 with mspIR in line with the Plac promoter. pCAB16 was linearize at a BsaAI site in mspIR, interrupting mspIR expression (which would otherwise be lethal) and thereby selecting for inserts by ligating into the BsaAI site (FIG. 7). The rsaIR PCR fragment was ligated into pCAB16, transformed into a RsaI methylase pre-modified *Ecoli* host. Colony PCR was performed on ten colonies; one isolate #9 contained the PCR rsaIR fragment. Sequencing showed correct DNA sequence for rsaIR matching the predicted N-terminal amino acid sequence of the 18 kDa protein. The pCAB16-rsaIR #9 was in the opposite orientation to Plac and mspIR, and when assayed showed detectable, but partial, RsaI restriction endonuclease activity.

The RsaI endonuclease gene (rsaIR) fragment from pCAB16-rsaIR #9 was gel purified following digestion with PstI and BamHI, and then ligated into pRRS. Transforming this ligation into separate *E.coli* hosts pre-modified with either the RsaI or the MjaV methylase failed to produce transformants carrying of an active RsaI restriction clone in pRRS.

Attempts to directly clone the RsaI restriction-modification system on a PCR fragment containing all three ORFs, rsaIM (ORF1), convergent unknown ORF rsaIU (ORF2), and rsaIR (ORF3) from *Rhodopseudomonas sphaeroides* chromosomal DNA into pUC19, also failed to yield an intact RsaI endonuclease. Only 3 pUC19 clones, #1, #6, and #12 were isolated that proved resistant to RsaI endonuclease digestion, and these contained a smaller deleted DNA fragment. DNA sequencing of #1 revealed an intact rsaIM gene with only part of the unknown gene rsaIU (ORF2) and all of rsaIR (ORF3) completely deleted.

Another attempt to establish an RsaI endonuclease clone involved the use of a plasmid pLT7K (NEB#1285, New England Biolabs, Inc., Beverly, Mass.) containing a highly regulated T7 promoter. pLT7K has the colE1 origin of replication compatible with both pSX20 and pIH919. The plasmid contains the PR promoter from phage lambda orientated against the IPTG regulated T7 promoter, and it also contains ampicillin and kanamycin resistance genes. The $P_R$ promoter is repressed at 30° C. by the lambda cI repressor. This repressor, the product of the phage lambda cI857 gene, is temperature sensitive and fails to repress $P_R$ above 37° C., allowing $P_R$ promoter expression. The Tn903-derived kanamycin gene is located in line with $P_R$ promoter with cloning sites on either side allowing for direct selection for inserts on plasmids which become Kan sensitive. At the other end is the opposing T7 promoter regulated by the lacI repressor which is induced by the addition of IPTG. The method for endonuclease gene overexpression using pLT7K is as follows: Plasmids containing an endonuclease gene in line with T7 promoter are grown at 37° C. to an OD590 0.8 to 1.0, allowing antisense expression from $P_R$ promoter which interferes with any expression of the endonuclease gene from the opposing T7 promoter. The culture temperature is lowered to 30° C., PR becomes repressed, then IPTG is added to induce the T7 promoter and the endonuclease gene. (ie.rsaIR)

Using Vent® DNA polymerase, the RsaI endonuclease gene (rsaIR) was PCR-amplified from pCAB16-rsaIR #9, and cloned following digestion with XbaI and XhoI, and ligation into pLT7K. The ligation reaction was tranformed into *E.coli* DH5α, which lacks the T7 RNA polymerase, and plated on LB+Amp plates containing 20 mM glucose at 37° C. Plasmid DNA was isolated from 18 kanamycin-sensitive colonies. Twelve contained the correct size rsaIR fragment as indicted by XbaI+XhoI double digestion. Four of these pLT7K-rsaIR clones were transformed into an RsaI methylase pre-modified *E.coli* ER2566 host containing T7 RNA polymerase. When assayed, the pLT7K-rsaIR clones showed varying amounts of detectable RsaI restriction endonuclease activity. The clone with the most RsaI endonuclease activity, #5-3 pLT7K-rsaIR showed the most RsaI endonuclease activity. Four individual colonies from #5-3 pLT7K-rsaIR plate were again grown and then IPTG-induced and assayed for RsaI endonuclease activity but this time, no RsaI endonuclease activity was detected, suggesting that the clone was unstable.

To create a stable over-expressing RsaI endonuclease clone one more step was found to be necessary, namely the use of an *E.coli* host pre-modified with both methylases, M.RsaI and M.MjaV. Using compatible vector plasmids containing these two methylases, a highly expressing RsaI endonuclease clone was established in *E.coli*. In order to do this, the RsaI methylase gene (rsaIM) was cloned onto pIH919, a derivative of pACYC184 containing the Plac promoter and polylinker from pUC18. The MjaV methylase gene (mjaVM) was cloned into pSX20, a derivative of pSC101 compatible with both pBR322 and pACYC-based plasmids. The pSX20-mjaVM methylase plasmid was then transformed into competent *E.coli* host ER2744 containing the pIH919-rsaIM plasmid. This *E.coli* host ER2744 strain, containing both methylases was made competent and was tranformed with the original miniprep DNA from pLT7K-rsaIR #5, described above. The host, *E.coli* ER2744, contains the T7 polymerase necessary for expression of the rsaIR from Thr T7 promoter.(Note: An attempt to clone an active RsaI restriction gene rsaIR directly into pRRS by transforming into this dual pre-modified *E.coli* host containing the M.RsaI and M.MjaV failed. Plasmid DNAs of twelve colonies from this transformation were isolated and no clones appeared to contain the correct size rsaIR insert or show detectable RsaI endonuclease activity.

Five colonies, from this transformation, were then grown at 37° C. to OD590 0.8 to 1.0, culture temperature was then lowered to 30° C., followed by IPTG induction. When asssayed for RsaI endonuclease activity, all five clones #51, #52, #53, #54 and #55 showed varying amounts of RsaI endonuclease activity, the highest being #51 at over $10^6$ u/g (FIG. 8). A glycerol stock of pLT7K-rsaIR #51 clone was stored at −70° C. #51 glycerol stock was later thawed, restreaked on LB ampicillin, chloramphenicol and kanamycin plates at 37° C. and again individual colonies were grown and induced at 30° C. and assayed for RsaI endonuclease activity. All four individual clones, including one such clone pKL167-51 expressed R.RsaI at more than $5\times10^6$ units of RsaI endonuclease produced per gram of wet *E.coli* cells. The recombinant RsaI endonuclease from pKL167-51 can be purified by chromatography to near homogeneity.

BRIEF DESCRIPTION OF THE DRAWINGS

FIG. 2. RsaI methylase gene (SEQ ID NO:1) and its encoded amino acid sequence (SEQ ID NO:2).

FIG. 3. RsaI endonuclease gene (SEQ ID NO:3) and its encoded amino acid sequence (SEQ ID NO:4).

FIG. 4. RsaI unknown gene (SEQ ID NO:5) and its encoded amino acid sequence (SEQ ID NO:6).

DETAILED DESCRIPTION OF THE INVENTION

Figure 1:
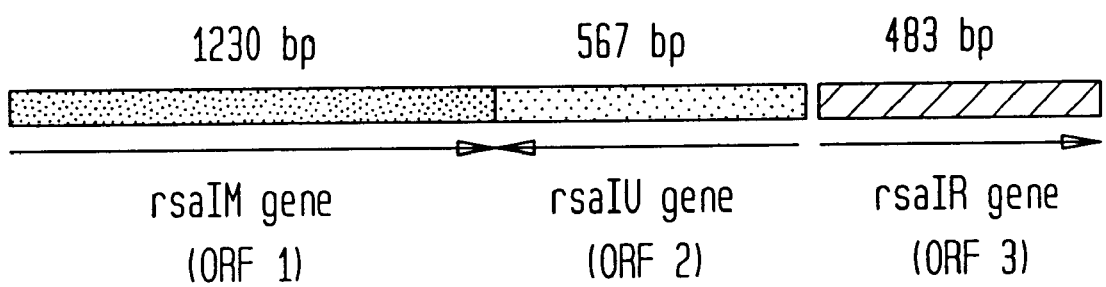
FIG. 1. Gene organization of RsaI restriction-modification system
Figure 5:
FIG. 5. A plasmid map of pIH919-rsaIM methylase clone.
Figure 6:
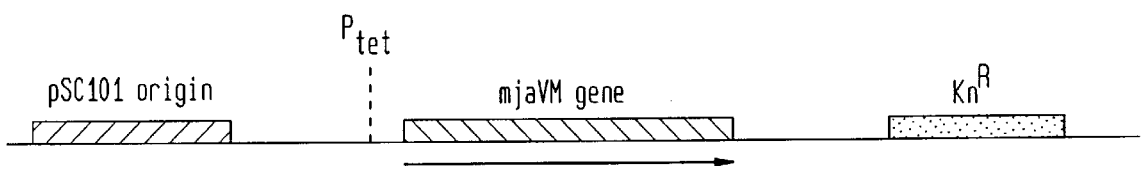
FIG. 6. A plasmid map of pSX20-mjaVM methylase clone.
Figure 7:
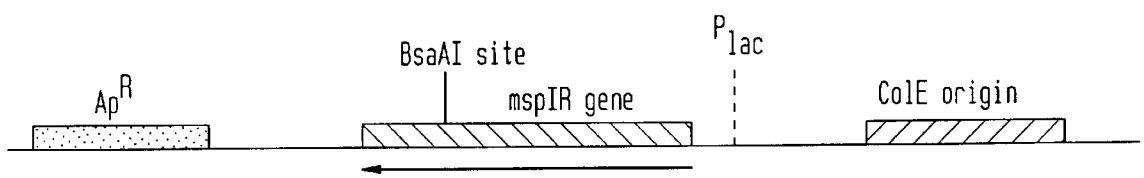
FIG. 7 A plasmid map of pCAB16.

In order to successfully overproduce the RsaI endonuclease from a clone, further steps beyond methylase selection were required including the use of a specially-repressed plasmid vector pLT7K, in an *E.coli* host pre-modified with two methylases, M.MjaV and M.RsaI. Two MTases were needed to completely protect *E.coli* DNA from RsaI digestion, and they were introduced into the host using two compatible plasmids, one containing rsaIM and the other mjaVM. These plasmids were transformed into an *E. coli* host containing T7 RNA polymerase, and this strain was then transformed with a third compatible plasmid pLT7K-rsaIR containing the rsaIR gene, followed by selection for colonies containing all three recombinant plasmids on antibiotic Luria-Broth plates.

The method described herein by which the RsaI methylase gene and the RsaI restriction endonuclease genes are preferably cloned and expressed in *E.coli* employs the following steps:

1. Construction of an ApoI Partial Genomic DNA Library

*Rhodopseudomonas sphaeroides* genomic DNA was digested with ApoI to achieve the desired partial digestion. The ApoI complete and partially digested genomic DNA in the range of 0.5–20 kb was ligated into EcoRI-cut and CIP-treated vector pBR322 at 17° C. overnight. Transformation was carried out using ER2418 *E.coli* competent cells and ligated DNA. The transformants were pooled and amplified. Plasmid DNA was prepared from the overnight cell cultures.

2. Challenge the ApoI Partial Library DNA with RsaI Digestion and Isolate of the RsaI Methylase Gene The ApoI partial library DNA was digested with RsaI at 37° C. for 2 hr. The digested DNA was transformed into ER2418 competent cells. Plasmid DNA was isolated from cell cultures of individual transformants. The individual plasmid DNAs were digested with RsaI to detect any resistance to digestion. Two plasmids, isolate #1 and #2, displayed complete resistance to RsaI digestion. These clones carried the cloned RsaI M gene.

3. Sequencing of the Insert Carrying the RsaI Methylase Gene

DNA sequencing verified the location of the inserted RsaI methylase gene (ORF1) within the insert and revealed a partial, converging, open reading frame (ORF2). When the complete ORF1 was compared to the known gene products in GenBank using BLAST, it showed homology to N4-methyl cytosine methylases. The complete ORF1 of 1230 bp encodes the RsaI methylase (409 amino acid molecular mass=45.4 kDa). The partial ORF2 showed no match to any of the known proteins in the Genbank data base.

4. N-Terminal Amino Acid Sequencing of Purified RsaI Restriction Endonuclease

The non-recombinant RsaI endonuclease was purified to near-homogeneity and subjected to SDS-PAGE. Two protein bands were detected with molecular masses of approximately 18 kDa and 22 kDa. The N-terminal amino acid sequence of the 18 kDa protein was determined to be (M)ERRFPLRW DEEELARAFKVTTK (SEQ ID NO:7). The N-terminal amino acid sequence of the 22 kDa protein was determined to be (M)AREIPDLQAVVRTGTGKGAARQARX (SEQ ID NO:8). (The 18 kDa protein sequence matches exactly with the predicted N-terminal amino acid sequence encoded by ORF3 as described in section 5. The 22 kDa sequence did not match any of the cloned ORFs. It was concluded that RsaI restriction endonuclease would most likely be the 18 kDa protein.)

5. Inverse PCR to Clone ORF2 and ORF3

*Rhodopseudomonas sphaeroides* genomic DNA was amplified by inverse PCR of self-ligated, HpaII- and NciI-cleaved DNA. The inverse PCR product was cloned following digestion with ApoI and PstI and ligation into pUC19. The ligation was transformed into a M.RsaI pre-modified strain. Plasmid DNAs were isolated from eight colonies and digested with ApoI and PstI. NciI #7, HpaII #2, #3, #4, and #7 contained an inverse PCR fragment. DNA sequencing of NciI #7 and HpaII #7 revealed 493 bp of new DNA sequence. The sequence confirmed the location of the ApoI site on the chromosome of *Rhodopseudomonas sphaeroides*, and completed the sequence of the converging open reading frame ORF2. The inverse PCR fragments included the ApoI site, thus containing new DNA from this ApoI site out to the HpaII/NciI site on the *Rhodopseudomonas sphaeroides* chromosome. (The HpaII site (CC/GG) overlaps the NciI site (CC/GGG)). The inverse-PCR fragment sequence also contained an ATG start codon and 102 bp of a new ORF running in the same direction as rsaIM. The derived amino acid sequence of the product of this new ORF (ORF3) included experimentally determined sequence of the 18 kDa candidate protein and 14 additional amino acids. When this new partial ORF (ORF3) was compared to known gene products in GenBank using BLAST, it did not match with known proteins in the Genbank data base. This is a typical feature of restriction endonuclease.

In the direction of the ApoI site, back towards rsaIM, a GTG start codon, proposed to be the beginning of the convergent unknown ORF2, was located 31 bp away from the beginning of ORF3 (rsaIR). This unknown ORF2 termed rsaIU, was originally assumed to be rsaIR; however, as described above, N-terminal R.RsaI endonuclease (18 kDa) protein sequence proved that this assumption was wrong, since the N-terminal 18 kDA protein sequence matched the beginning of ORF3 and not the beginning of ORF2. To identify the C-terminal end of R.RsaI, PCR primers were designed to PCR the 3' end of rsaIR excluding the ATG start of the gene to minimize any potential toxic expression of an intact rsaIR. Genomic DNA was amplified by inverse PCR of self-ligated, MfeI-cleaved DNA. The Vent® polymerase PCR product was digested with PstI, and cloned into pUC19 cut with SmaI and PstI, and then sequenced. The newly-derived sequence extended the total DNA sequenced to 2714 bp, including the sequence from the original ApoI fragment isolate #1, and the inverse PCR of the HpaII/NciI chromosomal fragment. Translation of this complete DNA sequence in all six reading frames indicated that there were two complete open reading frames downstream of the RsaI methylase gene: the unknown converging rsaIU (ORF2) and rsaIR (ORF3)(FIG. 1). The sequences of products of ORF2 and ORF3 did not match any of the known proteins in the Genbank data base.

6. Expression of the RsaI Methylase Gene in *E.Coli*

The entire RsaI methylase gene (1230 bp) was PCR amplified from genomic DNA using Vent® polymerase and two oligonucleotide primers to rsaIM. The PCR product was digested with KpnI and BamHI, ligated into pIH919 digested with KpnI and BamHI, and transformed into *E.coli* ER2502, and ER2566. The transformants were pooled and amplified. Plasmid DNA was prepared from an overnight culture and then digested with RsaI at 37° C. for 1 hour. The digested pool was re-transformed into ER2502 and ER2566. Individual plasmid DNAs were purified and digested with RsaI to detect resistance to RsaI digestion; four isolates, #1, #2, #4 and #6 contained the rsaIM PCR fragment and all appeared to be completely modified against RsaI digestion. #1 was then transformed into *E.coli* strains ER2566 and ER2744, and the transformants were made competent using standard CaCl$_2$ method.

7. Expression of the MjaV Methylase Gene in *E. Coli*

A 0.9 kb PCR fragment from *Methanococcus jannaschii* containing the mjaVM methylase gene was gel-purified, digested with BamHI and SalI, ligated into the BamHI- and Sa/I-cleaved pSX20, and then transformed into *E.coli*. The resulting pSX20-mjaVM plasmid DNA was purified and was shown to be completely modified against RsaI digestion. The pSX20-mjaVM plasmid was then transformed into *E.coli* strain ER2566 and made competent using standard CaCl$_2$ method. The pSX20-mjaVM plasmid was also transformed into competent *E.coli* ER2744 containing the pIH919-rsAIM plasmid (section 11).

8. Cloning of the Complete RsaI Restriction Endonuclease Gene

Two primers were synthesized for PCR-amplification of the rsaIR gene (ORF3) from *Rhodopseudomonas sphaeroides* chromosomal DNA. The PCR product was digested with PstI and BamHI, ligated into PstI- and BamHI-digested pRRS, and then transformed into *E.coli* strains ER2566 [pSX20-rsaIM] and ER2566 [pSX20-mjaVM]. The pSX20-rsaIM plasmid contained a subcloned DNA fragment from the original methylase clone, ApoI #1 (section 2).

Although both *E.coli* strains appeared to fully protected against RsaI digestion, only ER2566 [pSX20-rsaIM] cells yielded clones with RsaI endonuclease activity. Two clones out of twenty, isolates #13 and #14, contained the correct rsaIR fragment as detected by colony PCR, and showed some endonuclease activity. ER2566 [pSX20-mjaVM]

yielded no RsaI endonuclease clones from the same ligation. Minipreps of #13 and #14 were also transformed into ER2566 [pSX20-mjaVM] and re-assayed for RsaI endonuclease activity again. Several isolates of #14 showed varying amounts of RsaI activity with the highest amount of RsaI activity from cultures grown at 37° C. verses 30° C. DNA sequence of the reduced activity clone #14 revealed a deletion mutation of T at the start codon (ATG) which most likely truncated the RsaI endonuclease at the N-terminus leading to initiation at a later, downstream GTG codon. These truncated RsaI endonuclease clones exhibited little or no RsaI endonuclease activity when grown at 30° C., and partial activity when grown at 37° C.

The above mentioned undigested PCR of rsaIR (ORF3) was then blunt-end ligated into pCAB16 at the BsaAI site followed by transformation into ER2566 [pSX20-rsaIM] cells. One out of ten isolates, #9, contained the correct rsaIR fragment as detected by colony PCR. Sequencing showed correct DNA sequence for rsaIR, matching the predicted N-terminal amino acid sequence of the 18 kDa protein. The rsaIR gene in clone #9 was in the opposite orientation to Plac and mspIR, and when assayed the clone showed partial RsaI restriction endonuclease activity.

9. Expression of the RsaI Endonuclease Gene in *E.Coli* ER2566 [pIH919-rsaIM]

Since the pCAB16-rsaIR #9 clone contained the correct DNA sequence for rsaIR, an attempt was made to subclone the RsaI endonuclease gene from this plasmid into pRRS. Using flanking PstI and BamHI sites designed within the PCR primers, pCAB16-rsaIR #9 was digested with PstI and BamHI, and the resulting rsaIR gene fragment was gel-purified and ligated into PstI- and BamHI-digested pRRS. This ligation reaction was transformed into ER2566 [pIH919-rsaIM], and plasmid DNA was individually purified from 16 colonies. The plasmid DNAs were digested with PstI and BamHI to identify the rsaIR insert. None of the clones contained the rsaIR DNA fragment.

10. Expression of the RsaI Endonuclease in *E. Coli* Gene ER2566 [pIH919-rsaIM] using pLT7K Using Vent® DNA polymerase, the RsaI endonuclease gene (rsaIR) in pCAB16-rsaIR #9 was PCR-amplified digested with XbaI and XhoI, and ligated into pLT7K. The ligation reaction was transformed into *E.coli* DH5α. Plasmid DNAs were isolated from 18 colonies. Twelve contained the correct size rsaIR fragment as indicted by XbaI and XhoI double-digestion. Clones,#1, #4, #5, and #14 were transformed into a RsaI methylase pre-modified *E.coli* ER2566 host containing T7 RNA polymerase. The number of transformants varied between the four individual transformations of pLT7K-rsaIR clones: one for #14, three for #5, 1000 for #4, and 250 for #1. All the transformants from #5 and #14, and two for each #1 and #4 were inoculated, re-streaked and grown at 37° C. followed by induction with IPTG. When assayed, #1, #4, #5 and #14 rsaIR-pLT7K clones showed varying amounts of detectable RsaI restriction endonuclease activity. #5-3 pLT7K-rsaIR showed the most RsaI endonuclease activity. Four individual colonies from #5-3 pLT7K-rsaIR plate were again grown at 37° C., IPTG-induced and assayed for RsaI endonuclease activity. No RsaI endonuclease activity was detected, suggesting that the clone was extremely unstable.

11. Over-Expression of RsaI Endonuclease Gene in *E. Coli* Strain ER2744 [pIH919-rsaIM] and [pSX20-mjaVM]

Our failure to isolate and maintain clones overexpressing the RsaI endonuclease was judged to be a consequence of inadequate protection by the M.RsaI MTase. This problem was solved by the addition of a third plasmid containing an isoschizomer methylase M.MjaV MTase.

First, the RsaI methylase gene (rsaIM) was PCR-amplified and cloned onto pIH919, a derivative of pACYC184 containing the Plac promoter and polylinker from pUC18. The MjaV methylase gene (mjaVM) was cloned into pSX20, a derivative of pSC101 compatible with both pBR322 and pACYC-based plasmids. It has the pBR322 tetracycline resistance gene, pSC101 origin of replication, and a kanamycin resistance gene. The pSX20-mjaVM methylase plasmid was then transformed into competent *E.coli* ER2744 containing the pIH919-rsaIM plasmid. The resulting strain, containing both above mentioned methylases, was made competent. Note: An attempt to clone an active RsaI restriction gene (rsaIR) (ORF3) directly into pRRS by transforming into this dual pre-modified *E.coli* host containing the M.RsaI and M.MjaV failed. Twelve colonies from this transformation were isolated and no clones appeared to contain the correct size insert. Attempts to clone rsaIR using pLT7K into an *E.coli* strain containing the RsaI methylase alone failed to establish a stable RsaI endonuclease clone.

Figure 8:
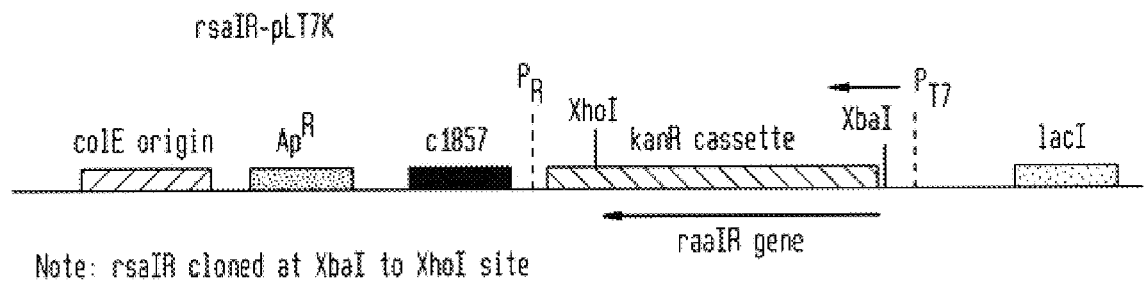
FIG. 8. A plasmid map of pLT7K-rsaIR endonuclease clone #5.

To finally establish an over-expressing RsaI endonuclease clone, the original miniprep DNA from pLT7K-rsaIR #5 (described above) was transformed into a T7 RNA polymerase containing *E.coli* host ER2744 pre-modified with two methylases, M.RsaI and M.MjaV. Five colonies were grown at 37° C. to OD590 0.8 to 1.0, culture temperature was then lowered to 30° C., followed by IPTG induction. When asssayed for RsaI endonuclease activity, all five clones #51, #52, #53, #54 and #55 showed various amounts of RsaI endonuclease activity, the highest amount of activity came from #51 at over $10^6$ u/g (FIG. 8). A glycerol stock of pLT7K-rsaIR #51 clone was stored at −70° C. #51 glycerol stock was later thawed, re-streaked on LB ampicillin, chloramphenicol and kanamycin plates at 37° C. and again individual colonies were grown and induced at 30° C. and assayed for RsaI endonuclease activity. All four individual clones, including one such clone pKL167-51 expressed R.RsaI at more than $5\times10^6$ units of RsaI endonuclease produced per gram of wet *E.coli* cells. The recombinant RsaI endonuclease from pKL167-51 is purified by chromatography to near homogeneity.

12. Purification of RsaI Restriction Endonuclease

The recombinant RsaI endonuclease was purified by standard protein purification techniques such as affinity chromatography, or ion-exchange chromatography.

The present invention is further illustrated by the following Examples. These Examples are provided to aid in the understanding of the invention and are not construed as a limitation thereof.

The references cited above and below are herein incorporated by reference.

EXAMPLE I

Cloning of RsaI Restriction-Modification System In *E.Coli*

1. Construction of an ApoI Partial Genomic DNA Library

Genomic DNA was prepared from *Rhodopseudomonas sphaeroides*, NEB Culture Collection #233, (Lynn el, *J. Bacteriol.* 142:380–383 (1980)). 7.5 μg of this genomic DNA was digested with 3, 1.5, 0.75, 0.375, 0.18, 0.09, 0.045, and 0.025 units/μg of ApoI at 50° C. for 1 hour to give a range of complete and partial digestion products. The tubes were incubated at 68° C. for 10 minutes to heat-kill the enzyme, then the digests were pooled. The pooled ApoI digested genomic DNA was ligated into EcoRI cut and CIP-treated vector pBR322 at 17° C. overnight followed by transformation into E.coli ER2418 and plated on LB+Amp (100 μg/ml). About 1000 colonies were obtained from transformation. To increase the number of colonies, a 3×transformation was again carried out using ER2418 cells and ligated DNA. About 5,000 transformants were obtained. All the transformants were pooled and inoculated into 500 ml of LB+Amp and incubated at 37° C. overnight. Plasmid DNA was prepared from the overnight cells by CsCl centrifugation.

2. Challenge the ApoI Partial Library DNA with RsaI Digestion and Cloning of the RsaI Methylase Gene 1 μg of the ApoI partial library DNA was digested with 30 units of RsaI at 37° C. for 2 hours. The digested DNA was transformed into ER2418 and plated on LB+Amp plates. Two transformants were obtained and plasmid DNAs were isolated from each individual transformant and digested with 10 units/μg of RsaI at 37° C. for 2 hours to detect any resistance to digestion. Both plasmids, #1 and #2 appeared to have complete resistance to RsaI digestion. Both contained two ApoI fragments of approximately 5.3 kb and 6.3 kb DNA.

3. Sequencing of the Insert Carrying the RsaI Methylase Gene

Deletion mapping and subcloning of the pBR322 ApoI #1 methylase clone showed that rsaIM was located on the 5.3 kb ApoI fragment. The deleted insert of #1 plasmid DNA was sequenced by primer walking by the dideoxy termination method using Ampli Taq DNA polymerase dye deoxy terminator sequencing kit and ABI373A automated DNA sequencer. DNA sequencing verified the location of the rsaIM gene (ORF1) and identified a partial converging open reading frame (ORF2). ORF1 of 1230 bp encoded the RsaI methylase (409 aa. molecular mass=45.4 kDa)(FIG. 2). The partial ORF2 did not match with known proteins in the GenBank data base.

4. N-Terminal Amino Acid Sequencing of the Purified RsaI Restriction Endonuclease The non-recombinant RsaI endonuclease was purified to near homogeneity and the purified protein was subjected to SDS-PAGE. Two protein bands (approximately 18 kDa and 22 kDa) were detected. The N-terminal amino acid sequence of the 18 kDa protein was determined as (M)ERRFQLRWDEEE LARAFKVTWK (SEQ ID NO:7). The N-terminal amino acid sequence of the 22 kDa protein was determined as (M)AREI PDLQAVVRTGTGKGAAR-QARX (SEQ ID NO:8). The 18 kDa protein sequence matches exactly with the predicted N-terminal amino acid sequence of ORF3 described in section 5. The 22 kDa sequence did not match any of the cloned ORF's. It was later concluded that RsaI restriction endonuclease would most likely be the 18 kDa protein.

5. Inverse PCR to Clone ORF2 and ORF3

To clone the missing portion of the ORF2, Rhodopseudomonas sphaeroides genomic DNA was amplified by inverse PCR. 10 μg of genomic DNA was cleaved with HpaII and 10 μg more was cleaved with NciI. Both digestions were performed at 37° C. for 1 hour, heat killed at 65° C. for 10 minutes, and, then placed on ice. Each of the two cleaved DNA samples was self-ligated at a low concentration (2 μg/ml) at 17° C. overnight, and used as templates for inverse PCR with the following two primers:
5' AGGTCCGGATCCATCGGATTGWIT1FGT-TGCAGCGGC 3' (C.rsaIM) (SEQ ID NO:9)

5' AGGTCCCTGCAGTTGGTGCCTTTGGAGC-CGTTATCC 3' (c.rsaIM) (SEQ ID NO:10)

PCR conditions of 95° C. 1', 55° C. 1', 72° C. 3', 25 cycles, were employed. Using Vent® (Exo-) polymerase an inverse PCR product of approximately 850 bp was generated in both cases. 1 μg of 850 bp PCR fragment was gel-purified from both reactions and digested with ApoI to verify the ApoI site within ORF2 of the original methylase clone #1. The ApoI site within ORF2 downstream of rsaIM dropped out an approximately 350 bp fragment generated by the C.rsaIM PCR primer. From this ApoI site outward, approximately 500 bp of new DNA was generated by the other inverse pcr primer c.rsaIM. Another 1 μg of gel-purified 850 bp PCR fragment from each reaction was then digested with ApoI and PstI (c.rsaIM PstI site) and ligated to ApoI- and PstI-cleaved pUC19 followed by transformation into E.coli ER2566 containing pSX20-rsaIM and plated on LB+Amp+Kan (100/50 μg/ml) and incubated at 37° C. overnight. Plasmid DNAs were isolated from 16 colonies, 8 from the HpaII reaction, and 8 from the NciI reaction. 1 μg of each plasmid was digested with ApoI and PstI and analyzed by gel electrophoresis. NciI #7, HpaII #2,3,4, and #7 contained an inverse pcr fragment. DNA sequencing of NciI #7 and HpaII #7 revealed 493 bp of new DNA sequence, and that the HpaII (CCGG) and NciI (CCGGG) sites coincided. This new sequence completed ORF2, and contained an ATG start codon and 102 bp of a new DNA open reading frame from (ORF3) running in the same direction as rsaIM. The first 20 amino acids of the protein encoded by this new ORF was identical to the observed N-terminal protein sequence of the 18 kDa candidate R.RsaI protein (section 4) indicating that this was the true start of the rsaIR gene.

To identify the C-terminal end of ORF3, another inverse PCR primer (R.Rsa.c) was designed to PCR the 3' end of rsaIR excluding the ATG start of the gene to minimize the potential toxicity of an intact rsaIR.

10 μg of genomic DNA was cleaved with MfeI at 37° C. for 1 hour, heat killed at 65° C. for 10 minutes, and then placed on ice. The MfeI-cleaved DNA was self-ligated at a low concentration (2 μg/ml) at 17° C. overnight and then used as the template in an inverse PCR reaction using a newly designed primer (R.Rsa.c) with (c.rsaIM) primer heading toward an MfeI site within rsaIM (ORF1):
5' AGGTCCCTGCAGTTGGTGCCTTTGGAGC-CGTTATCC 3' (c.rsaIM) (SEQ ID NO:11)
5' TGCGCGCGCCTTCAAGGTCACGAC 3' (R.Rsa.c) (SEQ ID NO:12)

The same inverse PCR conditions were employed as before. 1 μg of gel-purified PCR product was digested with PstI, ligated into SmaI- and PstI-cleaved pUC19 and then transformed separately into E.coli ER2683 and E.coli ER2566 [pSX20-rsaIM] and plated on LB+Amp or LB+Amp+Kan plates respectively. Plasmid DNAs were isolated from both ER2683 and ER2566 [pSX20-rsaIM] transformants. Two such clones, ER2683 #2-2, and ER2566 [pSX20-rsaIM] #5-4 were CsCl-purified and then sequenced. The newly-derived sequence from #2-2 and #5-4 extended the total DNA sequenced to 2714 bp and completed ORF3. Within this DNA were three large ORFs: the RsaI methylase gene, rsaIM, (ORF1); an unknown converging gene, rsaIU, (ORF2); and the gene finally identified as rsaIR, (ORF3) (FIG. 1). The rsaIR gene (ORF3) is 483 bp in length. It codes for a 160-aa protein of predicted MW of 18.7 kDa (FIG. 3), in agreement with the observed size of 18 kDa seen by PAGE.

6. Cloning of the RsaI Methylase Gene

In order to clone the entire complete RsaI endonuclease gene (rsaIR), an E.coli strain modified against RsaI endonuclease digestion was made by cloning rsaIM into a compatible pACYC184 derivative, pIH919. The entire methylase gene (1230 bp) was amplified from genomic DNA using Vent® polymerase with PCR conditions 95° C. 1' 54° C. 1', 72° C. 1', 30 cycles and two primers (5mRsaI) and (3mRsaI):
5' CGGGGTACCGCATGCAAGGAGGTT-TAAAATATGAACCAGCTCTCCA TGTTTGAC-CGAGTC 3' (5mRsaI) (SEQ ID NO:13)
5'TGGCGGCCGGGATCCTCACTAGTGC-CGCTGCAACAAAACAATCCG 3' (3mRsaI) (SEQ ID NO: 14)

The PCR fragment was digested at 37° C. for 1 hour with KpnI, extracted with phenol/CHCl$_3$ and precipitated with isopropanol. The rsaIM PCR fragment was then resuspended and digested with BamHI at 37° C. for 2 hours and phenol/CHCl$_3$-extracted, and precipitated again, then ligated at 17° C. overnight into KpnI- and BamHI-cleaved pIH919. The ligation was transformed into E.coli ER2502 and ER2566 plated on LB+chloramphenicol (25 µg/ml) at 37° C. for overnight. The transformants were pooled and amplified. Plasmid DNA was prepared from a 10 ml overnight culture and then each pool was digested with RsaI at 37° C. for 1 hour. The digested pool was transformed into ER2502 and ER2566 and individual plasmid DNAs from 8 colonies from each transformation and all appeared to be the correct size plasmid. Four isolates from each transformation, #1, #2, #4, and #6, were analyzed futher and found to contain the rsaIM PCR fragment, and all appeared to be completely modified against RsaI digestion. #1 was then transformed into E.coli strains ER2566 and ER2744 were made competent using standard CaCl$_2$ method.

7. Cloning of the MjaV Methylase Gene

Two primers were synthesized for PCR amplification of mjaVM. The entire MjaV methylase gene (879 bp) was amplified from genomic DNA using Vent® polymerase with PCR conditions 95° C. 1' 54° C. 1', 72° C. 1', 25 cycles and two primers (mj1498 Foward) and (mj1498 Reverse):
5' GTTGGATCCGTMTTMGGAGGTAAT-TCATATGGAGATAAATAA AATCTAC 3' (mj1498 Forward) (SEQ ID NO:15)
5'GTTGAATCCGTCGACTATTTAAATAAATGCATC 3' (mj1498 Reverse) (SEQ ID NO: 16)

An approximately 0.9 kb PCR fragment from Methanococcus jannaschii containing the mjaVM methylase gene was gel purified, digested with BamHI and SalI and then ligated into the BamHI- and SalI-cleaved pSX20 at 17° C. overnight. This reaction was transformed into E.coli and plated on LB+Kan (50 µg/ml) and incubated at 37° C. overnight. The pSX20-mjaVM plasmid DNA was purified and appeared to be completely modified against RsaI digestion. The pSX20-mjaVM plasmid was transformed into ER2744 [pIH919-rsaIM] and plated on LB+Kan+Cam Kan (50/25 µg/ml) plates at 37° C. ER2744 containing [pIH919-rsaIM] and [pSX20-mjaVM] plasmids was made competent using standard CaCl$_2$ method for overexpression (section 11).

8. Cloning of the Complete RsaI Restriction Endonuclease Gene

Two primers were synthesized for PCR amplification of the entire rsaIR gene (ORF3). The gene was amplified from genomic DNA using Vent® polymerase with PCR conditions 95° C. 1' 54° C. 1', 72° C. 3', 25 cycles and two primers (rsa.r5) and (rsa.3r-2):
5'TTGTTCTGCAGTMGGAGGTT-TAAAATATGGAAAGACGlTTTCAACTT CGGTGG 3' (rsa.r5) (SEQ ID NO:17)
5'TTGGGATCCTCAGTGCCGAATGTCCCG-GACCATGTC 3' (rsa.3r-2) (SEQ ID NO:18)

The PCR product was gel purified, digested with PstI and BamHI, ligated into PstI- and BamHI-cleaved pRRS, transformed into E.coli strains ER2566 [pSX20-rsaIM] and ER2566 [pSX20-mjaVM], and then plated on LB+Amp+Kan (100/50 µg/ml) plates at 37° C. overnight.

Even though both E.coli strains appear to completely protect against RsaI digestion, only ER2566 [pSX20-rsaIM] cells yielded clones with RsaI endonuclease activity. Two clones out of twenty isolates, #13 and #14 from ER2566 [pSX20-rsaIM] cells, contained the correct size rsaIR fragment. This was verified by colony PCR of twenty colonies using pUC19 universal primers #1233 and #1224 (New England Biolabs) as follows: Individual colonies were picked from the LB agar plates, placed in 100 µl of dH$_2$O, boiled 5 minutes and then each allowed to cool to room temperature. Direct or colony PCR conditions of 95° C. 10 sec, 62° C. 1', 72° C. 1', 30 cycles were employed using 2.5 µl of boiled DNA in a 50 µl reaction with Vent® (Exo-) polymerase. Only #13 and #14 from ER2566 [pSX20-rsaIM], contained the rsaIR fragment and when assayed showed low levels of RsaI endonuclease activity. When sequenced, #14 revealed a deletion mutation of T at the start codon (ATG).

The rsaIR PCR fragment from primers, rsa.r5 and rsa.3r-2, was then blunt-end ligated into pCAB16 at the BsaAI site followed by transformation into ER2566 [pSX20-rsaIM] and plated on LB+Amp+Kan plates at 37° C. overnight. Colony PCR of ten colonies identified one clone, #9, which contained the correct rsaIR fragment as detected by colony PCR. Sequencing of pCAB16-rsaIR #9 showed correct DNA sequence for rsaIR matching the amino acid sequence of the 18.7 kDa protein.

9. Expression of the RsaI Endonuclease Gene in E.Coli Strain ER2566 [pIH919-rsaIM] using pRRS The pCAB16-rsaIR #9 clone contained correct DNA sequence for rsaIR, so an attempt was made to subclone the RsaI endonuclease gene from this vector into pRRS, and to transform it into an RsaI-methylase pre-modified E.coli host. Using the flanking PstI and BamHI sites designed within the PCR primers, 10 µg of pCAB16-rsaIR #9 plasmid (section 8) was digested with PstI and BamHI at 37° C. for 2 hours, and the rsaIR insert was gel purified and ligated into PstI- and BamHI-cleaved pRRS. This ligation reaction was transformed into ER2566 [pIH919-rsaIM] and plated on LB+Amp+Cam plates at 37° C. Plasmid DNA's were purified from 16 colonies, and then digested with PstI and BamHI. None of the clones contained the desired rsaIR gene insert. The same ligation was transformed into ER2566 [pSX20-mjaVM], plated on LB+Amp+Kan plates at 37° C. 20 colonies were picked and analyzed by colony PCR using pUC19 universal primers, #1233, and #1224. Again, none of the isolates were found to contain the rsaIR gene insert.

10. Expression of the RsaI Endonuclease Gene in E.Coli Strain ER2566 [pIH919-rsaIM] using pLT7K Two primers were synthesized for PCR amplification of rsaIR for cloning into pLT7K. The entire RsaI restriction endonuclease gene (483 bp) was amplified from template pCAB16-rsaIR #9 using Vent® polymerase with PCR conditions 95° C. 1' 54° C. 1', 72° C. 1', 25 cycles and two primers (Xba5RT7) and (Xho3RT7):
5'TGGGGTCTAGAGGAGGTAA-CATATGGGMAGACGTTTTCAACTTCGGT GGGAT-GAGGAGGAGC 3' (Xba5RT7) (SEQ ID NO:19)
5'TTGGGTCTCGAGTCAGTGCCGAATGTC-CCGGACCATGTCACG 3' (Xho3RT7) (SEQ ID NO:20)

The rsaIR PCR product generated from pCAB16-rsaIR #9, was gel-purified, digested with XbaI and XhoI and then ligated into XbaI- and XhoI-cleaved pLT7K at 17° C. overnight. The ligation reaction was transformed into *E.coli* DH5α and plated on (pre-warmed 37° C.) LB+amp plates containing 20 mM glucose at 37° C. overnight. Plasmid DNAs were isolated from eighteen ampicillin resistant, kanamycin sensitive colonies. Twelve contained the correct size rsaIR fragment as indicted by XbaI and XhoI digestion. One clone, pLT7K-rsaIR #5 was transformed into an ER2566 [pIH919-rsaIM] and plated on LB+Amp/Cam (100/25 μg/ml) plates (pre-warmed to 37° C.) and incubated overnight at 37° C. Only 3 transformants were obtained. All three colonies, #5-1, #5-2, and #5-3, were re-streaked on pre-warmed LB+Amp/Cam plates and also inoculated into pre-warmed 10 ml cultures containing LB+Amp/Cam and grown at 37° C. overnight. 0.5 ml of the overnight cultures were diluted in pre-warmed 50 ml cultures containing LB+Amp/Cam grown at 37° C. and grown to an OD590 of between 0.8 and 1.0, IPTG was to added to 85 mg/L and induced at 30° C. for approximately 2 hours. When assayed, all three rsaIR-pLT7K clones showed detectable, but varying amounts of RsaI restriction endonuclease activity. pLT7K-rsaIR #5-3 showed the most RsaI endonuclease activity. Four individual colonies from pLT7K-rsaIR #5-3 plate (stored at 4° C.) were again grown at 37° C. and IPTG induced at 30° C. and re-assayed for RsaI endonuclease activity. No RsaI endonuclease activity was detected.

11. Over-Expression of RsaI Endonuclease Gene in *E. Coli* Strain ER2744 [pIH919-rsaIM]; [pSX20-mjaVM]

Figure 9:
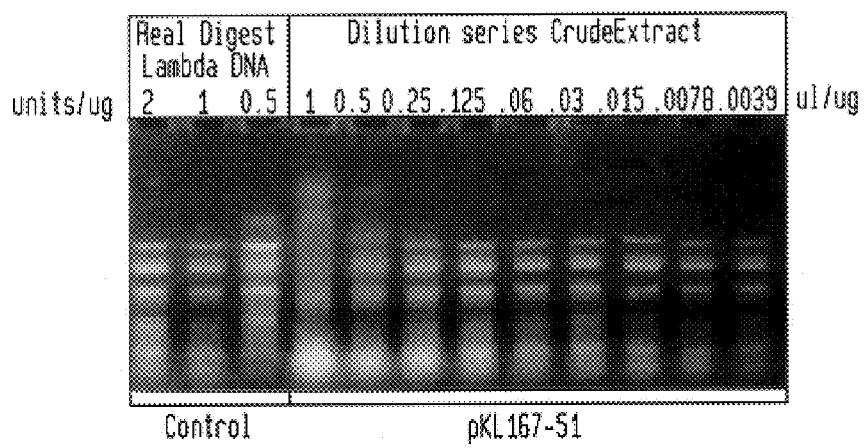
FIG. 9. Photogragh illustrating RsaI restriction enzyme activity from *E.coli* cell extract of pKL167-51.

Our failure to isolate and maintain expressing clones of the RsaI endonuclease in *E.coli* hosts carrying either the rsaIM gene or the mjaVM gene was judged to be a consequence of inadequate Mtase protection. Consequently, a new *E.coli* host was prepared that contained both Mtases, and when this host was transformed with rsaIR gene, a stable R.RsaI overexpressing clone was finally obtained. To finally establish this over-expressing RsaI endonuclease clone, the original miniprep DNA from pLT7K-rsaIR #5 (section 10) was transformed into a T7 RNA polymerase containing *E.coli* host ER2744 pre-modified with two methylases, M.RsaI and M.MjaV, plated on (37° C. pre-warmed) LB+Amp+Cam+Kan plates (100/25/50 μg/ml) and placed at 37° C. overnight. Five colonies, #51, #52, #53, #54 and #55, were inoculated into 10 ml (37° C. pre-warmed) LB+Amp+Cam+Kan and grown at 37° C. overnight. 1 ml of each overnight culture was inoculated into 50 ml of (37° C. pre-warmed) LB+Amp+Cam+Kan and grown to OD590 0.8 to 1.0, then the culture temperature was then lowered to 30° C., followed by IPTG (85 mg/L) induction at 30° C. overnight. When asssayed for RsaI endonuclease activity, all five clones, showed various amounts of RsaI endonuclease activity, the highest amount of activity came from #51 at over $10^6$ u/g (FIG. 8). A glycerol stock of pLT7K-rsaIR #51 clone was stored at −70° C. #51 glycerol stock was later thawed, re-streaked, on pre-warmed LB+Amp+Cam+Kan plates at 37° C. overnight. Four individual colonies were inoculated into 10 ml (37° C. pre-warmed) LB+Amp+Cam+Kan and grown at 37° C. overnight. 1 ml of each overnight culture was inoculated into 50 ml of (37° C. pre-warmed) LB+Amp+Cam+Kan and grown to OD590 0.8 to 1.0, then the culture temperature was then lowered to 30° C., followed by IPTG (85 mg/L) induction at 30° C. overnight. All four individual clones expressed R.RsaI at more 106 u/g. One such clone, pKL167-51, expressed R.RsaI at approximately $5 \times 10^6$ units of RsaI endonuclease produced per gram of wet *E.coli* cells. This assay was performed as follows: IPTG-induced cells were harvested, resuspended in 5 ml of sonication buffer, then lysozyme was added to 25 μg/ml, and the suspension was incubated on ice for 1 hour. 1 ml was sonicated for three, 10 second pulses and then clarified by centrifugation for 10 minutes at 4° C. The clarified cell extract was then assayed for RsaI endonuclease activity by mixing 1 μg λ DNA in 50 μl of reaction buffer with 1 μl of extract; 25 μl is removed and then diluted 2-fold each time though a series of 9 tubes and then incubated at 37° C. for 1 hour.(FIG. 9). The recombinant RsaI endonuclease from pKL167-51 is purified by chromatography to near homogeneity.

A sample of the *E. coli* ER2744 containing [pIH919-rsaIM, pSX20-mjaVM, pLT7K-rsaIR], (NEB#1242) has been deposited under the terms and conditions of the Budapest Treaty with the American Type Culture Collection on May 26, 2000 and received ATCC Accession Number PTA-1926.

10. Purification of RsaI Restriction Endonuclease

The recombinant RsaI restriction endonuclease is purified by standard protein purification techniques such as affinity chromatography, or ion-exchange chromatography.

What is claimed is:

1. Isolated DNA coding for the RsaI restriction endonuclease, wherein the isolated DNA is obtainable from *Rhodopseudomonas sphaeroides*.

2. A recombinant DNA vector comprising a vector into which a DNA segment encoding the RsaI restriction endonuclease has been inserted.

3. Isolated DNA encoding the RsaI restriction endonuclease and methylase, wherein the isolated DNA is obtainable from ATCC No. PTA-1926.

4. A cloning vector which comprises the isolated DNA of claim 3.

5. A host cell transformed by the vector of claim 2 or 4.

6. A method of producing RsaI restriction endonuclease comprising culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

PATENT NO.   : 6,210,945 B1
DATED        : April 3, 2001
INVENTOR(S)  : Keith D. Lunnen, Richard D. Morgan, Timothy Meixsell and Geoffrey G. Wilson It is certified that error appears in the above-identified patent and that said Letters Patent is hereby corrected as shown below:

ABSTRACT,
Line 5, after "modification" delete ","

Column 3,
Line 23, after "PCR" delete ","

Column 4,
Line 11, replace "a" with -- an --
Line 12, replace "a" with -- an --
Line 30, replace "a" with -- an --

Column 5,
Line 14, replace "PR" with -- $P_R$ --
Line 61, after "activity" insert -- ) --
Line 62, after "colonies" delete ","
Line 62, after "transformation" delete ","
Line 63, replace "PR" with -- $P_R$ --

Column 7,
Line 41, replace "a" with -- an --

Column 9,
Line 48, replace "a" with -- an --

Column 10,
Line 62, replace "(Lynn el," with -- (Lynn et al., --

Column 11,
Line 47, replace "VTWK" with -- VTTK --
Line 66, replace "WITIFGT-" with -- TTTTGT --

Column 13,
Line 39, replace "GTMTTM" with -- GTAATTAA --
Line 65, replace "GTMGG" with -- GTAAGG --
Line 66, replace " CGITTT" with -- CGTTTT --.

Column 14,
Line 64, replace "GGGMA" with -- GGAAA --

UNITED STATES PATENT AND TRADEMARK OFFICE
CERTIFICATE OF CORRECTION

PATENT NO. : 6,210,945 B1
DATED : April 3, 2001
INVENTOR(S) : Keith D. Lunnen, Richard D. Morgan, Timothy Meixsell and Geoffrey G. Wilson It is certified that error appears in the above-identified patent and that said Letters Patent is hereby corrected as shown below:

<u>Column 16,</u>
Line 4, delete "then" second occurrence
Line 17, after "was" delete "then"
Line 19, after "more" insert -- than --
Line 20, replace "106" with -- $10^6$ --
Line 31, replace "is" with -- was --.
Line 32, replace "though" with -- through --
Line 34, replace "is" with -- was --
Line 43, replace "is" with -- was --

Signed and Sealed this

Twenty-ninth Day of January, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,210,945 B1  
DATED : April 3, 2001  
INVENTOR(S) : Keith D. Lunnen, Richard D. Morgan, Timothy Meixsell and Geoffrey G. Wilson It is certified that error appears in the above-identified patent and that said Letters Patent is hereby corrected as shown below:

Column 7,
Line 25, replace "(M) ERRFPLRW" with -- (M) ERRFQLRW --

Column 27,
Line 3, replace "Met Glu Arg Arg Phe Pro" with -- Met Glu Arg Arg Phe Gln --

Signed and Sealed this

Second Day of July, 2002

Attest:

Attesting Officer

JAMES E. ROGAN
Director of the United States Patent and Trademark Office